US010499903B2

(12) United States Patent
Kennedy, III et al.

(10) Patent No.: US 10,499,903 B2
(45) Date of Patent: Dec. 10, 2019

(54) ANCHOR/IMPLANT DEPLOYMENT DEVICE AND TISSUE REPAIR METHODS RELATED THERETO

(71) Applicants: Smith & Nephew, Inc., Memphis, TN (US); James J. Kennedy, III, Mont Vernon, NH (US); Brendan Collins, Manchester, NH (US); Robert J. McCaffrey, Hillsborough, NH (US); Jon B. Taylor, Groton, MA (US)

(72) Inventors: James J. Kennedy, III, Mont Vernon, NH (US); Brendan Collins, Manchester, NH (US); Robert J. McCaffrey, Hillsborough, NH (US); Jon B. Taylor, Groton, MA (US)

(73) Assignee: Smith & Nephew, Inc., Memphis, TN (US)

( * ) Notice: Subject to any disclaimer, the term of this patent is extended or adjusted under 35 U.S.C. 154(b) by 222 days.

(21) Appl. No.: 15/513,848

(22) PCT Filed: Oct. 13, 2015

(86) PCT No.: PCT/US2015/055238
§ 371 (c)(1),
(2) Date: Mar. 23, 2017

(87) PCT Pub. No.: WO2016/061044
PCT Pub. Date: Apr. 21, 2016

(65) Prior Publication Data
US 2017/0281152 A1 Oct. 5, 2017

Related U.S. Application Data

(60) Provisional application No. 62/064,034, filed on Oct. 15, 2014.

(51) Int. Cl.
*A61B 17/04* (2006.01)
*A61B 17/00* (2006.01)
*A61B 90/00* (2016.01)

(52) U.S. Cl.
CPC .... *A61B 17/0401* (2013.01); *A61B 2017/003* (2013.01); *A61B 2017/0409* (2013.01); *A61B 2090/3987* (2016.02)

(58) Field of Classification Search
CPC .......... A61B 17/0401; A61B 2017/003; A61B 2017/0409; A61B 2090/3987;
(Continued)

(56) References Cited

U.S. PATENT DOCUMENTS 1,527,291 A 7/1923 Zorraquin
2,623,521 A 12/1952 Shaw
(Continued)

FOREIGN PATENT DOCUMENTS

CN 2553748 A 6/2003
CN 101730506 A 6/2010
(Continued)

OTHER PUBLICATIONS

International Preliminary Report on Patentability from related PCT Application No. PCT/US2016/018234 dated Aug. 22, 2017.
(Continued)

*Primary Examiner* — George J Ulsh
(74) *Attorney, Agent, or Firm* — Burns & Levinson, LLP; Joseph M. Maraia

(57) ABSTRACT

Featured is an inventive anchor/implant deployment device for use in repairing damage to tissue (e.g., meniscus) as well as tissue repair methods related thereto. Such an anchor/implant deployment device is advantageously configured and arranged so the deployment device is capable of making at least an in situ adjustment to the path of a needle portion
(Continued)

having the anchor(s)/implant(s); is capable of rotating such a needle portion or the portion extending into the tissue/meniscus so that the distal end entering into the tissue/meniscus is desirably oriented such as to, for example, minimize damage to tissue; and making the needle portion of the deployment device replaceable so as to allow the deployment device to be reloaded thereby making other portions of the deployment device reusable during a given, procedure.

10 Claims, 14 Drawing Sheets

(58) Field of Classification Search
CPC . A61B 17/04; A61B 17/0482; A61B 17/0469; A61B 17/0487; A61B 2017/00243; A61B 2017/00411; A61B 2017/00783; A61B 2017/00867; A61B 2017/0437; A61B 2017/0441; A61B 2017/045; A61B 2017/0464; A61B 2017/0496; A61B 2017/22038; A61F 2/2445; A61F 2220/0016; A61F 2230/0091; A61F 2210/0014; A61F 2/2466
See application file for complete search history.

(56) References Cited

U.S. PATENT DOCUMENTS

| | | | |
|---|---|---|---|
| 5,104,381 A | 4/1992 | Gresl et al. | |
| 5,137,509 A | 8/1992 | Freitas | |
| 5,320,608 A | 6/1994 | Gerrone | |
| 5,401,247 A | 3/1995 | Yoon | |
| 5,509,910 A | 4/1996 | Lunn | |
| 5,569,288 A | 10/1996 | Yoon | |
| 5,573,511 A | 11/1996 | Yoon | |
| 5,578,053 A | 11/1996 | Yoon | |
| D379,515 S | 5/1997 | Kuehn et al. | |
| 6,001,084 A | 12/1999 | Rick et al. | |
| 6,071,292 A | 6/2000 | Makower et al. | |
| 6,270,484 B1 | 8/2001 | Yoon | |
| 6,656,160 B1 | 12/2003 | Taylor et al. | |
| 6,837,878 B2 | 1/2005 | Smutney et al. | |
| 3,202,251 A1 | 6/2012 | Bierman et al. | |
| 2002/0099335 A1 | 7/2002 | Zohmann | |
| 2003/0220677 A1 | 11/2003 | Doan et al. | |
| 2004/0133124 A1 | 7/2004 | Bates et al. | |
| 2004/0171986 A1 | 9/2004 | Tremaglio, Jr. et al. | |
| 2004/0225180 A1 | 11/2004 | Junger | |
| 2005/0159762 A1 | 7/2005 | Nuutinen | |
| 2006/0089609 A1 | 4/2006 | Bleich et al. | |
| 2008/0188928 A1 | 8/2008 | Salahieh et al. | |
| 2009/0157099 A1 | 6/2009 | Surti | |
| 2009/0163934 A1 | 6/2009 | Raschdort et al. | |
| 2009/0275970 A1 | 11/2009 | Leibowitz | |
| 2009/0287236 A1 | 11/2009 | Bakos et al. | |
| 2009/0299400 A1 | 12/2009 | Wayman et al. | |
| 2010/0036361 A1 | 2/2010 | Nguyen et al. | |
| 2010/0113873 A1 | 5/2010 | Suzuki et al. | |
| 2010/0160731 A1 | 6/2010 | Giovannini et al. | |
| 2010/0249750 A1 | 9/2010 | Racz | |
| 2011/0082538 A1 | 4/2011 | Dahlgren et al. | |
| 2011/0218485 A1 | 9/2011 | Tran et al. | |
| 2011/0224742 A1 | 9/2011 | Weisel et al. | |
| 2011/0257581 A1 | 10/2011 | Koziczynski et al. | |
| 2013/0211427 A1 | 8/2013 | Castell | |

FOREIGN PATENT DOCUMENTS

| | | |
|---|---|---|
| EP | 2149339 A2 | 1/2010 |
| EP | 2277457 A1 | 1/2011 |
| GB | 2064963 A | 6/1981 |
| GB | 2397235 A | 7/2004 |
| JP | S56-101305 U | 8/1981 |
| JP | H08-511711 A | 12/1996 |
| JP | H09-103433 A | 4/1997 |
| JP | 2012179087 A | 9/2012 |
| JP | 2013013592 A | 1/2013 |
| SU | 1232236 A1 | 5/1986 |
| SU | 1303149 A1 | 4/1987 |
| SU | 1560143 A1 | 4/1990 |
| WO | 94/06681 A3 | 11/1994 |
| WO | 95/00189 A1 | 1/1995 |
| WO | 2001006938 A1 | 2/2001 |
| WO | 2009114833 A1 | 9/2009 |
| WO | 2012006161 A2 | 1/2012 |
| WO | 2012096816 A1 | 7/2012 |

OTHER PUBLICATIONS

International Preliminary Report on Patentability from related PCT Application No. PCT/US2015/055238 dated Apr. 18, 2017.
International Search Report and Written Opinion from related PCT Application No. PCT/US2015/055238 dated Feb. 15, 2016.
European Application No. 15797481.7-1111 Office Action dated Jun. 4, 2019.

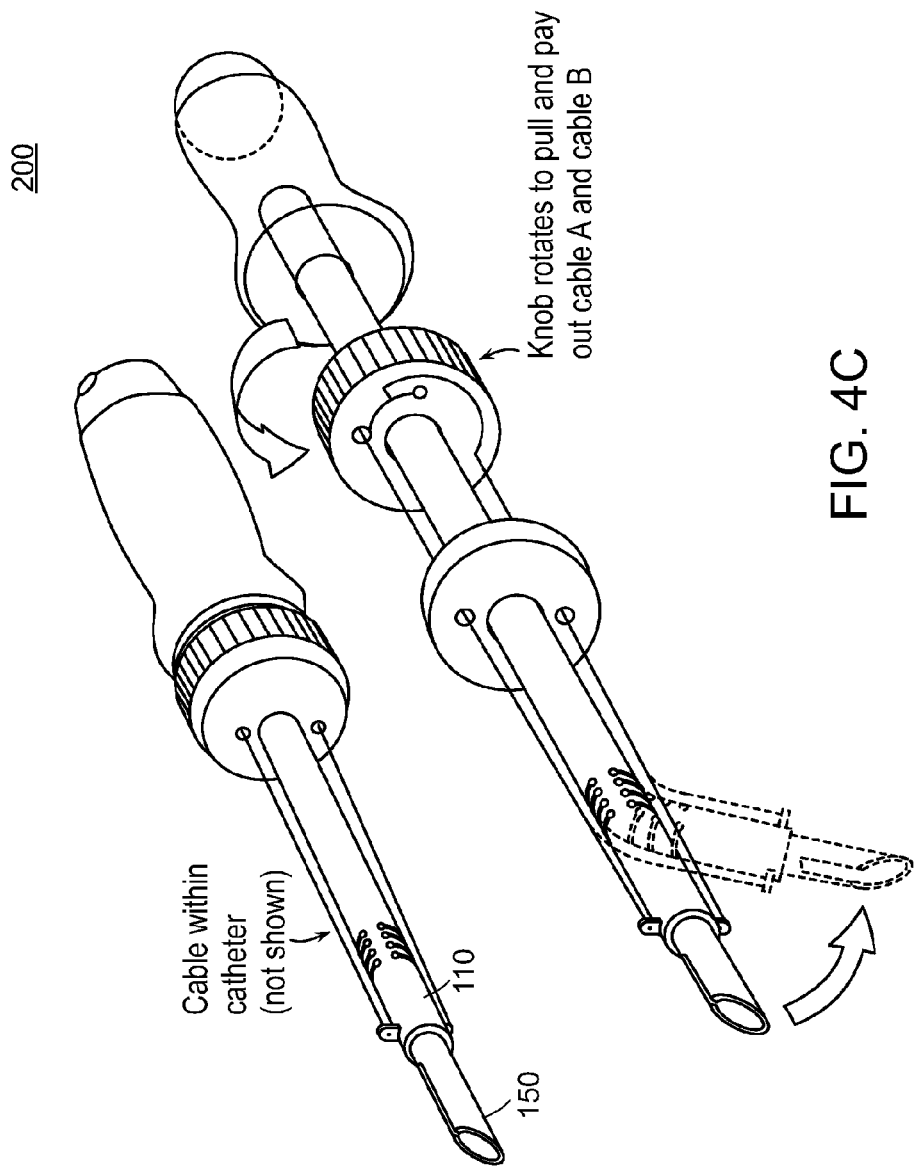

T1 T2 Deployment Mechanism Detail

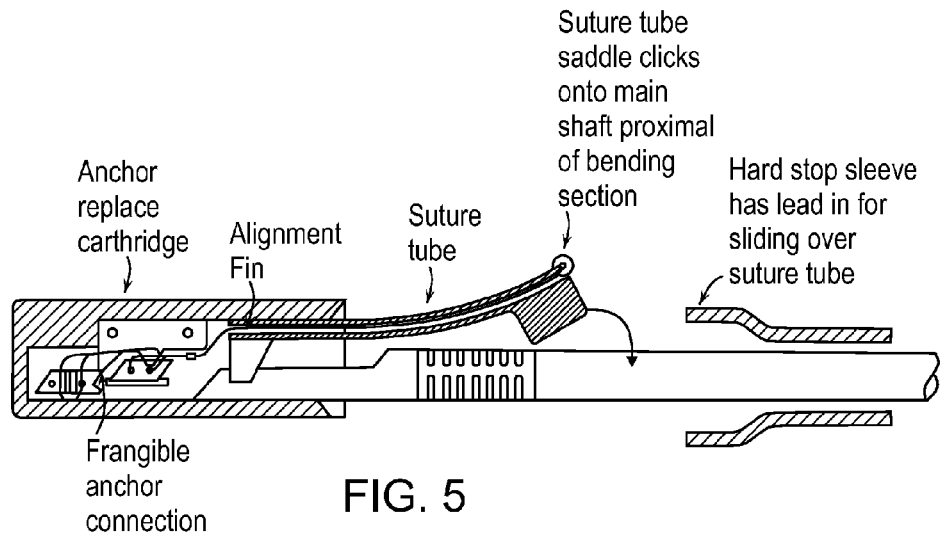
FIG. 5
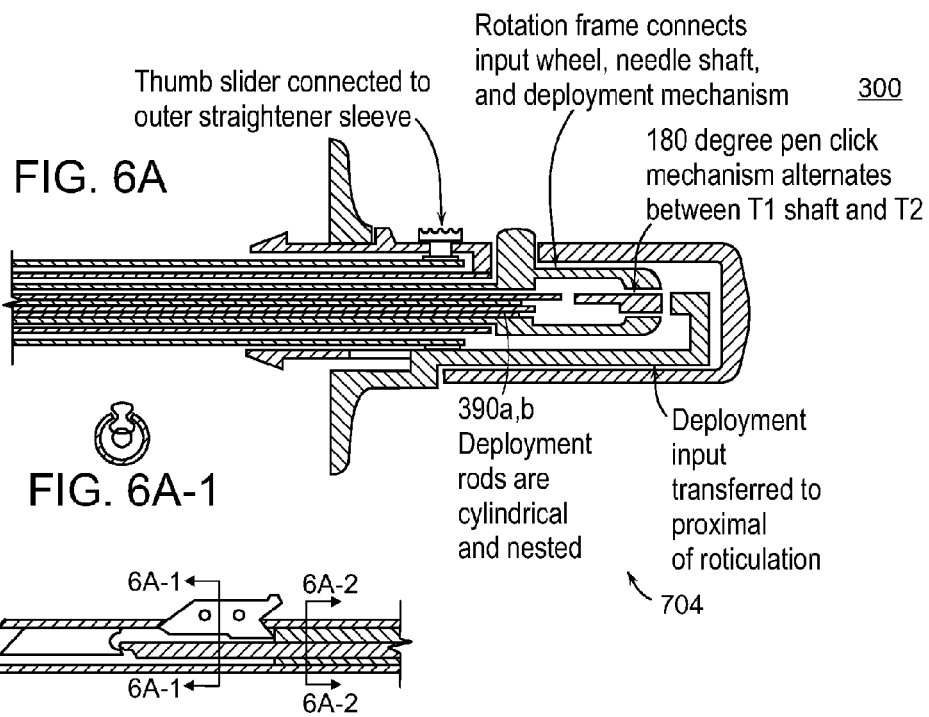
FIG. 6A
FIG. 6A-1
FIG. 6A-2

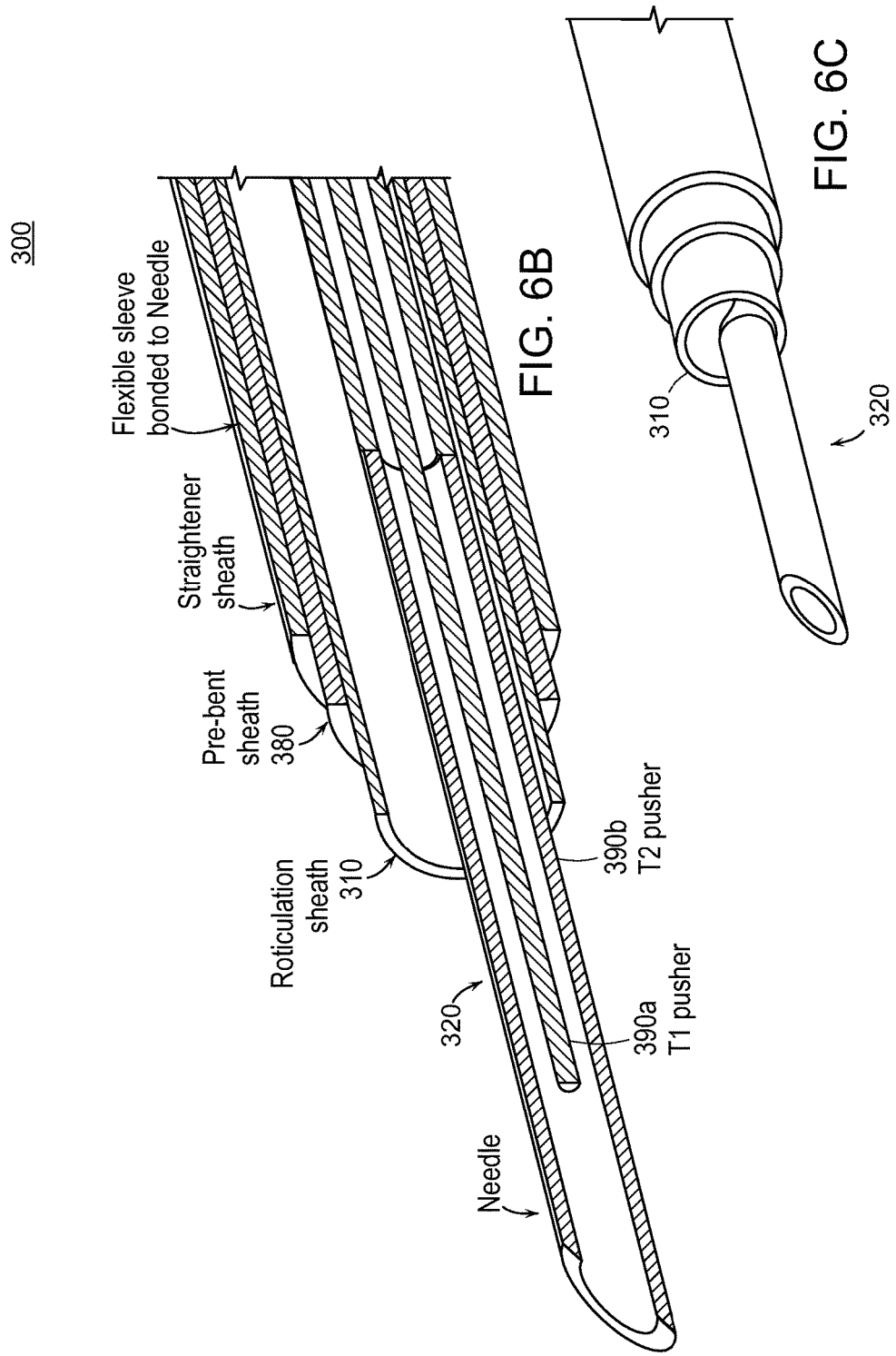

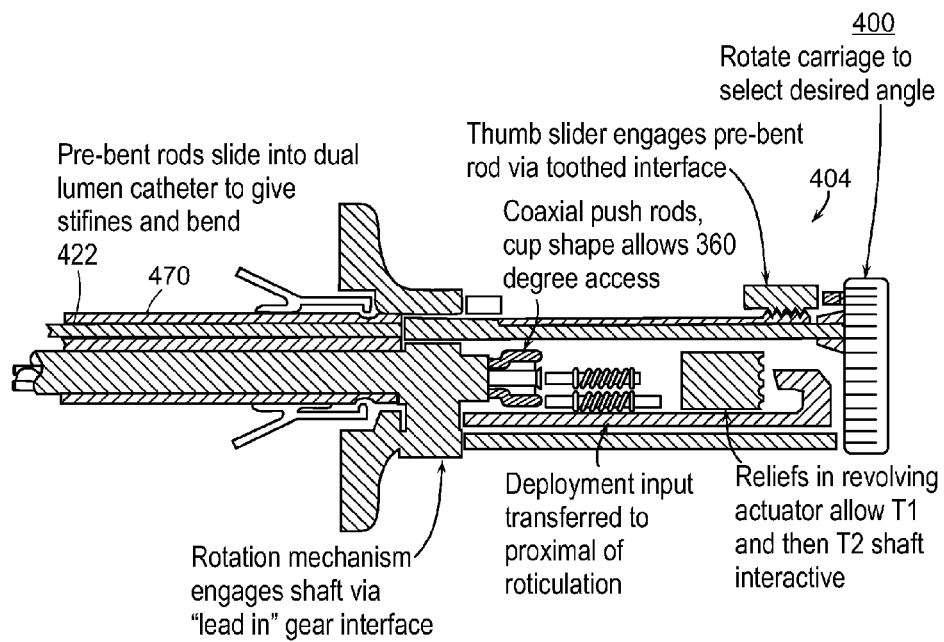
FIG. 8A
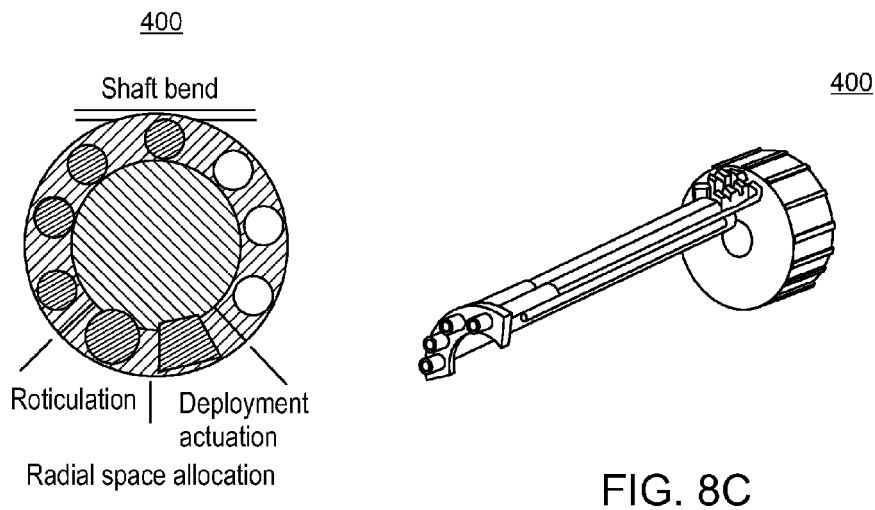
FIG. 8B
FIG. 8C

ANCHOR/IMPLANT DEPLOYMENT DEVICE AND TISSUE REPAIR METHODS RELATED THERETO

CROSS-REFERENCE TO RELATED APPLICATIONS

This application is the U.S. national phase entry under 35 U.S.C. § 371 of International Application No. PCT/US2015/055238, filed Oct. 13, 2015, entitled ANCHOR/IMPLANT DEPLOYMENT DEVICE AND TISSUE REPAIR METHODS RELATED THERETO, which in turn claims priority to and benefit of U.S. Provisional Application No. 62/064,034, filed Oct. 15, 2014, the contents of which are incorporated herein by reference in their entirety for all purposes.

FIELD OF INVENTION

The present invention relates to surgical devices for use in connection with surgical endoscopy procedures and in particular, in arthroscopy procedures and more particularly to an anchor implant deployment device having in-situ directional adjustability and surgical procedures or methods for repairing tissue including the meniscus using such a deployment device.

BACKGROUND OF THE INVENTION

The knee joint is formed from three bones, the femur (thighbone), the tibia (shinbone) and the patella (knee cap). Also and referring now to FIG. 1, there are two wedge-shaped pieces of cartilage that are positioned between the femur and tibia, which act as shock absorbers. These pieces of cartilage are called the meniscus and are tough and rubbery to help cushion the knee joint and keep it stable.

Meniscal tears are amongst the most common injuries to the knee. Sports-related meniscal tears also often occur along with other injuries to the knee such as tears or damage to the anterior cruciate ligament. However, people can experience a non-sports related meniscal tear or undergo a degenerative meniscal tear. For example, the cartilage can weaken and wear thin over time and such aged, worn tissue is more prone to tearing. As a result an awkward twist by a person when getting up from a chair may be enough to cause a meniscal tear, if weakened by age.

Meniscal tears can be treated in a number of different ways including (a) a nonsurgical treatment regime and/or (b) a surgical treatment regime. The type of treatment plan depends upon a number of factors including the type of tear one has, its size and location. For example, a tear(s) in a certain region of the meniscus may not heal effectively and thus the damaged piece(s) of the meniscus may be surgically trimmed away using an arthroscopic technique. In addition to the type of tear, other factors to consider include the age of the person, their activity level and any other related injuries that would need to be factored into the person's treatment plan (e.g., tears or injuries to the ACL).

If nonsurgical treatment does not appear to be effective (e.g., symptoms persist) or it is determined from the outset that nonsurgical treatment is not a viable option, then the doctor may recommend surgical treatment of the affected knee using any of a number of techniques and devices that are known in the art. Typically, an arthroscopic surgical technique is utilized along with various surgical instruments that have been developed for use in the technique to trim and/or repair the damaged tissue.

There are a number of meniscal repair procedures available for treating such damaged tissue that are commonly referred to as "all inside" meniscal repair procedures. These procedures have been found to be relatively easy to use to repair meniscal tears found in the posterior and middle segments of the meniscus; although such procedures require the surgeon to steer around nerves and tissue such as the ACL and PCL so as to reach the targeted area. However, the related repair devices are generally not capable of reaching tears in areas of the anterior segment of the meniscus. Consequently repairs in the anterior segment can involve techniques that require a surgeon to access the anterior and posterior regions of the knee to fully access and repair tears in the anterior segment. Also, such procedures are more difficult and also increase the risk of injury to surrounding tissue, muscle and nerves by the surgical devices.

There are a number of devices and techniques known in the art that have been developed for the surgical treatment of meniscal tears. A number of these techniques and related devices involve piercing the meniscus at one or more locations proximal to a tear with a needle carrying one or more anchors or implants that are coupled to a suture, deploying the anchor or implant at a back surface or side of the meniscus, withdrawing the deployment device and repeating the process to deploy any other anchors/implants. After all of the anchors/implants are deployed the surgeon using the appropriate technique, tightens the suture so as to draw the pieces comprising the tear together so they can heal over time.

The anchor or implant is typically made from a material that will eventually be absorbed over time or not absorbed overtime (e.g., PEEK). There are some techniques, however, in which a portion of a suture is used to form an anchor or implant (e.g., using a ZipLoop manufacturing technique). In this all suture technique, the deployment device is operated so that the portion of the suture forming the anchor/implant is deployed on the back side of the meniscus.

In these techniques, the anchor/implant deployment device usually embodies a sheath or cannula that is disposed about a needle member that carries the anchors/implants. The sheath or cannula is used to protect the person from inadvertent injury that could be caused by the needle member coming into contact with the surrounding tissue and the like, as well as to protect the anchor/implant and related sutures from coming into contact with the tissue and the like during insertion which could cause an inadvertent deployment. In use, the needle member is positioned in proximity to a targeted site of the meniscus so that the needle can be caused to pass through the meniscus and so that an anchor/implant can be appropriately deployed from the needle member.

The cannula and/or the needle member are typically arranged to have any one of a number of fixed geometries including a straight or a curved geometry. In use, the surgeon selects the geometry that is believed to best suited for reaching the targeted site without causing further injury to the patient, from the portal or entry site made in the skin and tissue proximal the knee joint such as when using an arthroscopic technique. In one technique the cannula is malleable so that the surgeon can bend the cannula in a desired manner.

There is another technique that uses a deployment device having two needle members that are arranged so that both pierce the meniscus at the targeted site. A suture is then deployed from the ends of two needle members proximal the back side of the meniscus. After withdrawing the needle members from the meniscus, the suture is arranged so that it extends along the back side of the meniscus and through the meniscus. The surgeon using the appropriate technique, tensions the suture to draw the tear together and to secure the suture in place.

After tightening the suture using any of the above described suture based techniques, the surgeon takes the appropriate actions to cut off the excess length of the suture. In exemplary embodiments, the surgeon typically inserts a suture cutter into the knee joint or capsule and advances the suture cutter along the suture to a particular point where the surgeon actuates a device (e.g., suture cutter) to cut off the excess length of suture.

There is found in U.S. Publication No. 2003/0139754 (which corresponds to U.S. Pat. No. 8,409,250), a system and surgical methods for repairing tears in meniscal tissue using meniscal darts. The system includes a cannulated insertion sheath, a meniscal dart, and a disposable dart driver preloaded with the meniscal dart at its distal end. According to the methodology, the insertion sheath is inserted into the meniscus such that a tip of the sheath is located near a meniscal tear. The dart driver with a preloaded dart is advanced through the insertion sheath such that the pre-loaded meniscal dart at the driver's distal end is inserted through the meniscal tear and so it remains disposed within the meniscus. The meniscal dart is used alone and without a suture to fix the meniscal tear.

There is found in U.S. Publication No. 2012/0239086, a suture anchor and delivery system, a method for attaching sutures to body tissue, a suture anchor for use in non-linear, non-collinear or divergent angle deployment and a control rod for a suture anchor and delivery assembly. The phrase non-linear, non-collinear or divergent angle deployment is understood to mean or describe a method and device where the suture anchor is deployed at an angle with respect to the long axis of the insertion device, guide or insertion cannula. This means that the long axis of the insertion device or cannula is not configured and arranged so the long axis is generally pointing in the direction of the targeted area. The suture anchor is designed with a curved body and beveled tip to facilitate its engagement with a tunnel (or hole) that is formed in a bone or cartilage support surface. The suture anchor is used in combination with an insertion device, guide or insertion cannula and a control rod so that the suture anchor can be inserted into the tunnel.

There is found in U.S. Publication No. US2004/0162559 (which corresponds to U.S. Pat. No. 6,875,219), instruments, systems and methodology for nonlinear access to bone tissue sites. More particularly, there is provided a bone access system offering radial access to sites with reduced user risk and ease of use. The system employs a flexible (semi-rigid) conduit that is formed into a curved shape by a curved core wire once the end of each item is advanced beyond the end of a cannula which restrains the core member (via the intermediately-located conduit). The core wire has a relatively low stiffness so it is easily set within the cannula (either together with the conduit or after the conduit has been placed therein). It is further provided that the conduit is for delivering material or a medical device to the site and that the core member is able to steer the conduit and allow the combination to be advanced thorough cancellous bone (cancellous bone is found in the interior of bones of the human skeleton).

There is found in U.S. Pat. No. 6,074,395, implant devices, instruments and methods for repairing body tissue during endoscopic surgical procedures such as those used when repairing meniscal tissue during arthroscopic surgery of the knee. As further described the instruments and methods are for inserting into a site of implantation, elongated devices having transversely extending barbs or projections which assist in retaining the implant in place within a tissue defect (e.g., a tear) and to hold body tissue in close approximation for healing or other reasons. Such elongated devices also are arranged so as to include a bore that extends lengthwise (longitudinal extending bore).

There is found in U.S. Publication No. 2008/0228204 (which corresponds to U.S. Pat. No. 8,257,371), medical suturing devices, systems, and methods that can be used in endoscopic (with or without access ports) or other surgeries in which access is limited, including open and minimally invasive surgical techniques. Articulation motions by the surgeon may be transferred from a handle to needle grasping jaws using an axial movement of a shaft that has axial stiffness (such as being stiff in compression) and lateral flexibility or an axial movement of a cable and such motions may be used to manipulate a needle so as to allow the surgeon to form stitches with the needle. Such a device can include an extension body (within which the shaft or cable moves) between the handle and jaws that can be pre-bent or custom bent by the user. Portions of the devices may be disposable, replaceable, and/or reusable. It also is provided that the device can include one or parts that can be disposable.

There is found in U.S. Publication No. 2013/0296989, an implanter 10 for nerve stimulation that includes a plurality of preformed stylets and a hollow needle. Also found is a method for introducing an implant for stimulating a nerve using the implanter. The implants may include electrical electrodes (leads), catheters, waveguides, laser and optical fibers, and mechanical, thermal, and chemical sensors, as well as medications, radiation seeds, viral vectors, chemicals, and other suitable materials. The hollow needle carrying the preformed stylet is inserted into a target region such as a subcutaneous region. Such a target region may be positioned within a brain or within a spine.

There is found in U.S. Publication No. 2012/0253116, a surgical system that includes a reusable handle assembly having a controller (e.g., a joystick controller); a reusable cannula assembly configured to be operatively connected to and steerable by the reusable handle assembly; and a plurality of surgical instruments. The surgical instruments are configured so as to be inserted through the reusable handle assembly and configured to advance a length of the reusable cannula assembly, and such that the plurality of surgical instruments are engaged with at least one trigger mechanism of the reusable handle assembly. Also, the handle assembly, the cannula assembly, and the plurality of surgical instruments are modular components configured to be releasably connected or coupled to each other.

It is further provided that a distal end of the reusable cannula assembly 120 includes a plurality of articulation linkages, which may be equally spaced apart from each other. The articulation linkages may be flexible segments, which are of equal length relative to each other or which are of different length relative to each other. The plurality of articulation linkages, distally disposed, facilitate the bending of a portion of the surgical instrument via the controller. Also, the reusable cannula assembly may include linkages that are not controlled by the controller which may define a pre-set bend actuated by operating switch.

There is found in U.S. Publication No. 2009/0138095 (which corresponds to U.S. Pat. No. 8,246,692), a method for treating a cartilage defect by implanting a cartilage replacement implant through an arthroscopic access. Such a method includes determining at least one parameter for describing the arthroscopic access, providing surgical instrumentation including at least two different applicator instruments for grasping the cartilage replacement implant, choosing one of the at least two applicator instruments of the instrumentation in dependence upon the at least one parameter determined for describing the arthroscopic access, and grasping and inserting the cartilage replacement implant into the patient's body with the chosen instrument through the arthroscopic access.

There is found in U.S. Publication No. 2012/0053641 (which corresponds to U.S. Pat. No. 8,801,716), methods for repairing cartilage in a patient as well as systems for repairing such cartilage. Such a system is for repairing, harvesting, and placement of cartilage (e.g., a cartilage plug including both cartilage and attached bone tissue). More specifically, the system (i.e., the trephine) can harvest the cartilage plug from a donor site and then using a guide tool and the ejector tool can be used to place the harvested plug at the defect site.

It thus would be desirable to provide a new deployment device that can deploy anchors/implants and which deployment device has the capability to adjust the end geometry of such a device and methods related thereto. It would be particularly desirable to provide such a device that would be capable of adjusting the end geometry and thus the path of the deployment device either when outside of the body and/or when in-situ or within the body. It also would be desirable to provide such a deployment device that would not increase the difficulty of using such a device or require an increase in the skill level of those using such devices.

SUMMARY OF THE INVENTION

In its broadest aspects the present invention features an inventive anchor/implant deployment device for use in repairing damage to tissue (e.g., the meniscus) as well as tissue/meniscus repair methods related thereto. Such an anchor/implant deployment device is advantageously configured and arranged so the deployment device is capable of making at least an in situ adjustment to the path of a needle portion having the anchor(s)/implant(s); is capable of rotating such a needle portion or the portion extending into the tissue/meniscus so that the sharp distal end entering into the tissue/meniscus is desirably oriented so as to minimize damage to tissue; and making the needle portion of the deployment device replaceable so as to allow the deployment device to be reloaded thereby making other portions of the deployment device reusable during a given procedure.

Allowing the deployment device to make at least an in situ adjustment to the path of a needle portion having the anchor(s)/implant(s) is particularly beneficial as this allows the needle portion to access many portions of the meniscus including the anterior portions of the meniscus that are not generally reachable by conventional all inside repair types of devices. It is within the scope of the invention for an adjustment to the needle portion to be made before the deployment device is inserted into the tissue/meniscus so that the needle portion is oriented for such insertion into the body including the knee joint. This is generally the case because such all inside repair types of devices have fixed geometries.

Such in situ adjustment to the path of a needle portion allows the deployment device of the present invention to minimize the potential for damaging tissue, nerves and other structures of a knee while portions of the deployment device are being maneuvered with the knee joint to the targeted repair site. In addition, such in situ adjustment also includes altering the geometry of the distal end of the deployment device so that the distal end can have different geometries suitable for reaching a targeted area while the distal end is being inserted (e.g., already disposed within the body). Such insertion also can be performed while minimizing risk of damage to the tissue, nerves, cartilage, ligaments and the like.

For example, the distal end of the deployment device can present a straight geometry as the distal end is being inserted into the body and to a given position with the body/knee joint. The distal end then can be re-configured so as to present a desired geometry, where the continued insertion of the anchor/implant occurs along the path defined by the desired geometry and so that the distal end can reach the targeted area.

In this way, a surgeon can select a geometry for the distal end that is appropriate or best suited for insertion into the body and into some portion of the body/knee joint and then re-adjust the geometry of the distal end so it is more appropriate for reaching the targeted repair site while at the same time minimizing risk of injury or damage to the surrounding tissue. This is advantageous over existing conventional all-inside repair devices that employ a fixed geometry for the device used to deliver the anchor/implant to the backside of the meniscus. In comparison, for devices with fixed curved geometries the surgeon has to carefully manipulate the device from the outset to minimize the risk of damage to the surrounding tissue, nerves, ligaments and the like.

According to one aspect of the present invention, such a deployment device is usable for deploying an anchor/implant such as for use in a procedure when treating damaged tissue. In more specific embodiments, such a deployment device is particularly suitable for insertion into the knee joint such as for the treatment of the tissues of a damaged meniscus. More particularly, such a deployment device includes a first member having a lumen extending along the longitudinal axis, a second member that is moveably disposed within the first member lumen and a moving mechanism that is operably coupled or connected to the first member.

Such a moving mechanism also is configured so as to cause the first member to present one of a plurality of end geometries and so as to control the extent or amount of movement by the first member responsive to the moving mechanism. In further embodiments, such a moving mechanism is arranged so that such moving of the first member occurs one of external to a body or in-situ within the body.

In yet further embodiments, the plurality of end geometries include a straight geometry, a bending geometry that bends in a first direction, another bending geometry that bends in a second direction (that is different from or opposite to the first direction), an arcuate or curved geometry that curves in a first direction, an arcuate geometry that curves in a second direction (that is different from or opposite to the first direction). Also, the moving mechanism is further configurable and arranged so as to control the extent or amount of bending or curving of the first member and also so as to maintain the straight end geometry of the first member.

In yet further embodiments the second member is coupled or connected to the first member and the first member includes a flexible portion that moves responsive to the moving mechanism. Also, the first and second members are further configured and arranged such that movement of the first member flexible portion with respect to the longitudinal axis is imparted to the second member thereby causing the second member to move in the direction of the first member responsive to the action of the moving mechanism. Further, such coupling or connecting of the first and second members is such that the extent of movement in the given direction by the second member is related to the extent of movement of the first member with respect to the longitudinal axis.

In yet further embodiments, the second member includes a distal end portion which carries one or more anchors/implants for deployment and a shaft portion, where the second member distal end portion and the shaft portion are configured so that the second member distal end portion is removably secured to the shaft portion and so that a new distal end portion, which is loaded with new anchors/implants for deployment, can be thereafter secured to the shaft member portion. In other words, the deployment device is configured and arranged so that it can be re-loaded with new anchor/implants. More particularly, the distal end portion is removably secured to the shaft member portion such that a used distal end portion (a distal end portion where the anchors/implants have been deployed) can be removed and replaced by a new distal end portion (a distal end portion which has anchors/implants to be deployed).

In yet further embodiments, the moving mechanism includes a rod that is secured to the first member and which rod is arranged so that it extends along a length of the first body member and so as to be disposed off-axis. In other words, the rod is spaced a distance from the long axis of the first member.

In yet further embodiments, the moving mechanism further includes a manipulation device that is operably coupled to the rod and arranged so that movement of the manipulation device in a given direction causes the rod to move axially and thus move the first member. In more particular embodiments, movement of the rod in one direction causes the first member to present one end geometry and movement of the rod in a second direction causes the first member to present a second end geometry.

In yet further embodiments, such a deployment device further includes a rotation device that is operably coupled to the second body member such that operation of the rotation device causes a distal end of the second body member to be rotated about its long axis. As a result of such rotation, the distal end is orientated in a desired angular orientation. More particularly, the distal end is configurable so as to present an end surface that can facilitate insertion of the second body member into the tissue as well as minimizing damage to such tissue during such an insertion. Thus, such rotation can be performed so that the end surface is orientated so as to minimize damage and/or facilitate insertion.

According to yet another aspect of the present invention, there are featured methods for treating damaged tissue such as tissues of the knee joint including the meniscus. Such methods include providing a deployment device that is configured and arranged so that one or more anchors/implants can be deployed from a distal end portion thereof, where the distal end portion also is configured and arranged so as to be adjustable, at least in-situ, so that the distal end portion can present one of a plurality of end geometries. Such a deployment device also can embody any of the features as herein described for such a deployment device. Such methods also include selecting one of the plurality of geometries; controlling the deployment device so the distal end portion thereof presents a desired one of the geometries and inserting the deployment device into the body (e.g., knee joint) and manipulating the deployment device so as to navigate the distal end portion within the body. It should be recognized that such selecting and controlling can be performed prior to insertion of the deployment device into the body or particular body part such as a knee joint as well as during the insertion of the deployment device.

While inserting the deployment device, such methods further include determining if the geometry of the distal end portion should be adjusted so that it can be navigated to a targeted location and if said determining concludes that the end geometry should be adjusted, then such methods include selecting another one of the plurality of geometries and thereafter controlling the deployment device so the distal end portion presents the another one of the plurality of geometries.

Such methods further include further manipulating the so-adjusted deployment device until the distal end portion is proximal the targeted tissue location and when the distal portion is so located, deploying the anchor/implant from the deployment device. As further described herein, such deploying can include passing the distal end portion through tissue at or about the targeted site so that the part of the distal end portion containing the anchor/implant is at a pre-deployment position. More particularly, when the tissue to be treated is that of the meniscus, the pre-deployment position is proximal the backside of the meniscus.

In yet further embodiments, such methods include determining if another anchor/implant should be deployed after said deploying. If another anchor/implant is to be deployed, then manipulating the so-adjusted deployment device until the distal end portion is proximal another targeted tissue location and when the distal portion is so located, deploying the anchor/implant from the deployment device.

In yet further embodiments, such methods further include, determining if another anchor/implant should be deployed after said deploying and determining if the so-adjusted deployment device has another anchor implant for deployment. If it is determined that the inserted deployment device does not have another anchor/implant to deploy then such methods further include withdrawing the inserted deployment device from the body, detaching the distal end portion from the second member, and attaching a new distal end portion to the second member. Thereafter, the user or surgeon repeats the steps of selecting and controlling, inserting, determining if the geometry of the distal end portion should be adjusted while it is being inserted, manipulating the so-adjusted deployment device so its proximal yet another targeted site and deploying the anchor/implant.

In the case, where it is determined that the deployment device does have another anchor to deploy then such methods further includes manipulating the so-adjusted deployment device until the distal end portion is proximal another targeted tissue location, and when the distal portion is so located, deploying the anchor/implant from the deployment device.

In yet further embodiments, such methods further include rotating the second member so that an end surface of the second member distal end portion is oriented to a desired arrangement for insertion of the distal end portion into tissue.

In yet further embodiments, the plurality of end geometries being selected includes one of a straight geometry, a bending geometry that bends in a first direction, another bending geometry that bends in a second direction (that is different from or opposite to the first direction), an arcuate or curved geometry that curves in a first direction, an arcuate geometry that curves in a second direction (that is different from or opposite to the first direction). In yet more particular embodiments, such selecting and controlling further includes controlling the extent or amount of bending or curving of the first member and controlling the deployment device so as to maintain the straight end geometry.

In yet further embodiments, such inserting of the distal end portion includes inserting the distal end portion of the deployment device into the knee joint such as for treatment of the meniscus. Also, such manipulating includes manipulating the distal end portion when disposed within the knee joint. Further, such deploying includes passing the distal end portion through the meniscus at the targeted site location so that the anchor/implant when deployed resides along he backside of the meniscus.

Other aspects and embodiments of the invention are discussed below.

Definitions

The instant invention is most clearly understood with reference to the following definitions:

USP or USP No. shall be understood to mean U.S. Patent Number and U.S. Publication No. shall be understood to mean U.S. Published Patent Application Number.

The terms "comprising" and "including: as used in the discussion directed to the present invention and the claims are used in an open-ended fashion and thus should be interpreted to mean "including, but not limited to." Also the terms "couple" or "couples" is intended to mean either an indirect or direct connection. Thus if a first component is coupled to a second component, that connection may be through a direct connection, or through an indirect connection via other components, devices and connections. Further the terms "axial" and "axially" generally mean along or substantially parallel to a central or longitudinal axis, while the terms "radial" and "radially" generally mean perpendicular to a central, longitudinal axis.

Additionally directional terms such as "above," "below," "upper," "lower," etc. are used for convenience in referring to the accompanying drawing figures. In general, "above,' "upper," "upward" and similar terms refer to a direction toward a proximal end of an instrument, device, apparatus or system and "below," "lower," "downward," and similar terms refer to a direction toward a distal end of an instrument, device, apparatus or system, but is meant for illustrative purposes only and the terms are not meant to limit the disclosure.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIGS. 4A-F are various views of an anchor/implant deployment device according to a second aspect of the present invention.

FIG. 5 is a cross-sectional view illustrative of the distal end of the deployment device of FIGS. 4A-F when coupled to a re-load device.

FIGS. 6A-F are various views of an anchor/implant deployment device according to a third aspect of the present invention.

FIG. 7A, is illustrative cross sectional view of the distal end of the deployment device of FIGS. 6A-F when coupled to a re-load device

FIGS. 8A-E are various views of an anchor/implant deployment device according to a third aspect of the present invention.

DESCRIPTION OF THE PREFERRED EMBODIMENT

Figure 1:
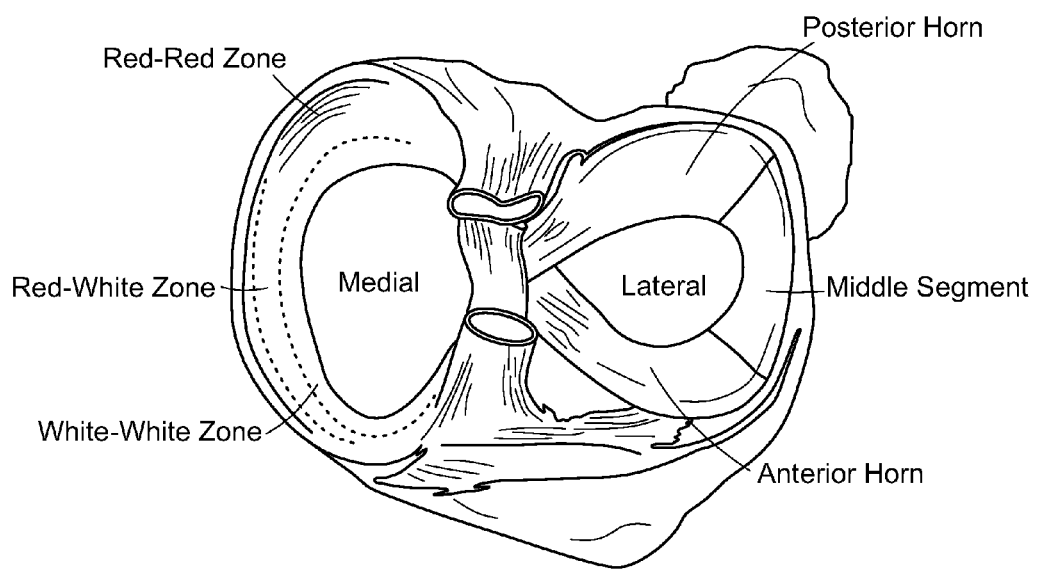
FIG. 1 is an illustrative view of a knee joint showing the meniscus.

Referring now to the various figures of the drawing wherein like reference characters refer to like parts, there is shown in FIGS. 2A-D various views of an anchor/implant deployment device 100 according to one aspect of the present invention. As described herein, such an anchor/implant deployment device 100 can be used in repairing damage to tissue and more particularly, the meniscus. As further described herein, such an anchor/implant device is also suitable for use in tissue repair methods such as the repair of the meniscus. As further described herein, such an anchor/implant deployment device 100 also is configurable so that it can allow the deployment device 100 to make an in situ adjustment to the path of a needle portion 154 thereof having the anchor(s)/implant(s) 120; allowing the deployment device 100 to rotate the needle portion or the portion extending into the meniscus so that the distal end (e.g., sharp distal end) thereof entering into the meniscus is oriented, such as for example, to minimize damage to tissue; and making the needle portion 154 of the deployment device replaceable so as to allow the deployment device to be re-loaded with new anchors/implants thereby making other portions of the deployment device reusable during a given surgical procedure.

Such allowing the deployment device 100 to make in situ adjustment to the path of a needle portion 154 having the anchor(s)/implant(s); allows the needle portion to access many portions of the meniscus including the anterior portions of the meniscus that are not generally reachable by conventional all inside repair types of devices. This is generally the case because such all inside repair types of devices use instruments having fixed geometries.

Such in situ adjustment to the path of a needle portion also allows the deployment device 100 to minimize the potential for damaging tissue, nerves and other structures of a knee (e.g., ACL or PCL) while portions of the deployment device are being maneuvered with the knee joint to the targeted repair site. In addition, such in situ adjustment also includes altering the geometry of the distal end 102 of the deployment device so that the distal end can have different geometries suitable for reaching a targeted area as the distal end is being inserted. Such insertion also can be performed while minimizing risk of damage to the tissue, nerves, cartilage, ligaments and the like.

For example, the distal end 102 of the deployment device can be arranged so as to present a straight geometry as the distal end is being inserted into the body and to a given position with the body/knee joint. The distal end 102 then can be re-configured so as to present another desired geometry (e.g., curved geometry), where the continued insertion of the anchor/implant occurs along the path defined by the curved geometry and so that the distal end 102 can reach the targeted area.

In this way, the surgeon can select a geometry for the distal end 102 that is appropriate or best suited for insertion into the body and into some portion of the knee joint and then re-adjust the geometry of the distal end so it is more appropriate for reaching the targeted repair site while at the same time minimizing risk of injury or damage to the surrounding tissue. This is advantageous over existing conventional all repair devices that employ a fixed geometry for the device used to deliver the anchor/implant to the backside of the meniscus. In comparison, for devices with fixed curved geometries the surgeon has to carefully manipulate the device from the outset to minimize the risk of damage to the surrounding tissue, nerves, ligaments and the like for example by the curved distal end.

In a particular aspect, the deployment device 100 includes a handle assembly 104, a first body member 110 that extends from the handle assembly and a second body member 150 moveably disposed with the first body member and which also can extend from the handle assembly. The first body member 110 includes at least a flexible portion 116. Such a deployment device 100 also includes a flexing mechanism 112, 114 that is operably coupled to the flexible portion 116 and the handle assembly 104, a rotating mechanism 130 operably coupled to the second body member that allows the second body member 150 to be rotated about its long axis. The second body member 150 also is flexible so that it allows a pathway to be defined by the flexible portion 116 of the first body member but has sufficient axial rigidity so it can pass through the tissue/meniscus and so that the anchor(s)/implant(s) 120 can be deployed therefrom.

The flexing mechanism 112, 114 is configured so as to cause the flexible portion 116 of the first body member 110 to be maintained in a straight geometry, a bending geometry that bends in a first direction or bends in a second direction (different from or opposite to first direction), or an arcuate or curved geometry that curves in a first direction or curves in a second direction (that is different from or opposite to the first direction). More particularly, such bending or curving occurs in the same plane, however, it is within the scope of the present invention for such bending and curving to be in different planes.

In one particular embodiment, a stiff wire or rod 112 (see FIG. 2A) is secured to the flexible portion 116 and so that it extends within the first body member 110 from the flexible portion, along the length of the first body member, to the handle assembly 104. More specifically, the wire or rod is arranged so it is disposed off-axis (i.e., it is spaced a distance from the long axis of the first body member). Because of the off-axis placement, an axially applied push or pull force to the flexible portion 116 or first body member by the wire/rod 112 causes the flexible portion to bend in either a first direction or a second direction. If no force is being applied, the flexible portion is generally maintained in a straight configuration.

In another particular embodiment, such a flexing mechanism includes a plurality of wires 112a that extend within the first body member and along the length of the first body member and are secured to the first body member so as to cause such bending. Such wires also are coupled to a device/mechanism in the handle assembly 104 which when manipulated by a surgeon causes the wires to move longitudinally in the appropriate manner so the first body member flexible portion moves in the desired direction. This arrangement is similar to that used for steering catheters.

Also, the stiff wire or rod 112 is connected to a mechanism or device disposed in the handle assembly such that when the mechanism is manipulated by the surgeon an axial push or pull force is applied to the wire/rod. The amount of bending in either direction is controllable by controlling the axial force being applied by such manipulation by the surgeon. In more specific embodiments, the axial force can be controlled so the flexible portion can bend in either direction (+ or − about the long axis) and in the range of from about +45 deg. to about −30 deg. It also is contemplated that the flexible portion can be bent in the range of from about +30 deg. to about −45 deg. It is further contemplated that the angular displacements with respect to the longitudinal axis can be adjusted to present other ranges of bending.

In further embodiments, the handle assembly includes an actuator 114 or slide that moves in the longitudinal direction. Also, the actuator 114 is operably coupled to the wire/rod 112 such that when the surgeon pushes the actuator in one direction (e.g., forward direction), the wire/rod is moved in the first direction and when moved in a second direction (e.g., reverse or backward direction) the wire/rod is moved in the second direction.

In further aspects/embodiments, the first body member is arranged so as to include a bending region corresponding to the flexible portion 116. This flexible portion or bending region can be arranged using any of a number or devices or techniques known to those skilled in the art. In illustrative embodiments, the flexible portion is a flexible extrusion or a laser cut tube. For example, the first body member can be made of a material such as a metal which includes a laser cut portion near the distal end of the first body member (see FIG. 2B), which allows the first body member 110 to bend in either direction in this region with respect to the longitudinal axis when the axial force is applied by the wire/rod.

Figure 2A:
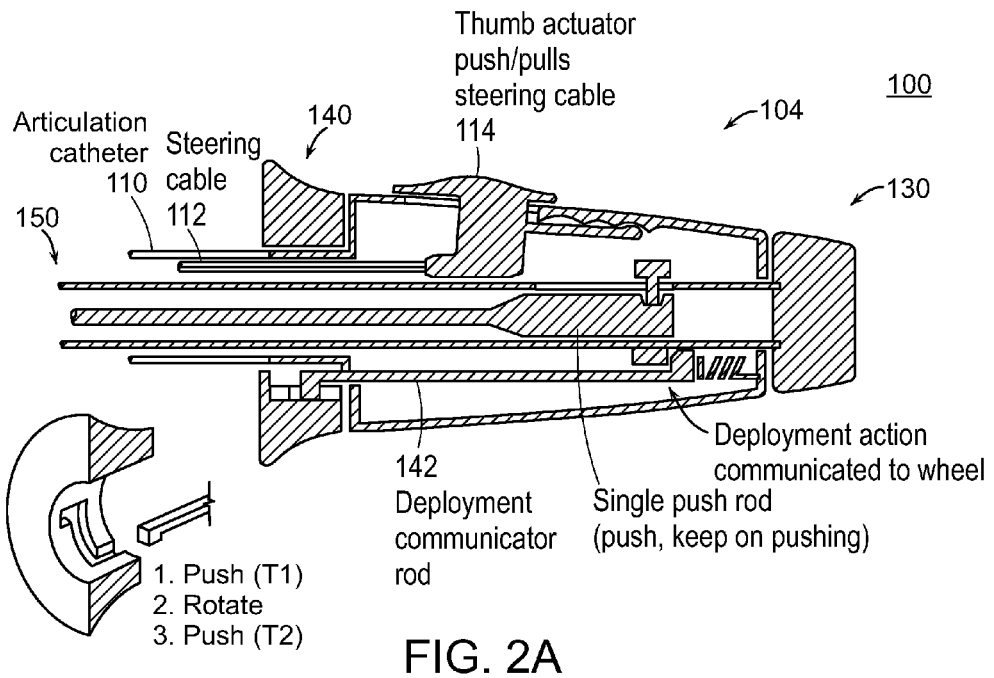
FIGS. 2A-D are various views of an anchor/implant deployment device according to one aspect of the present invention.
Figure 2B:
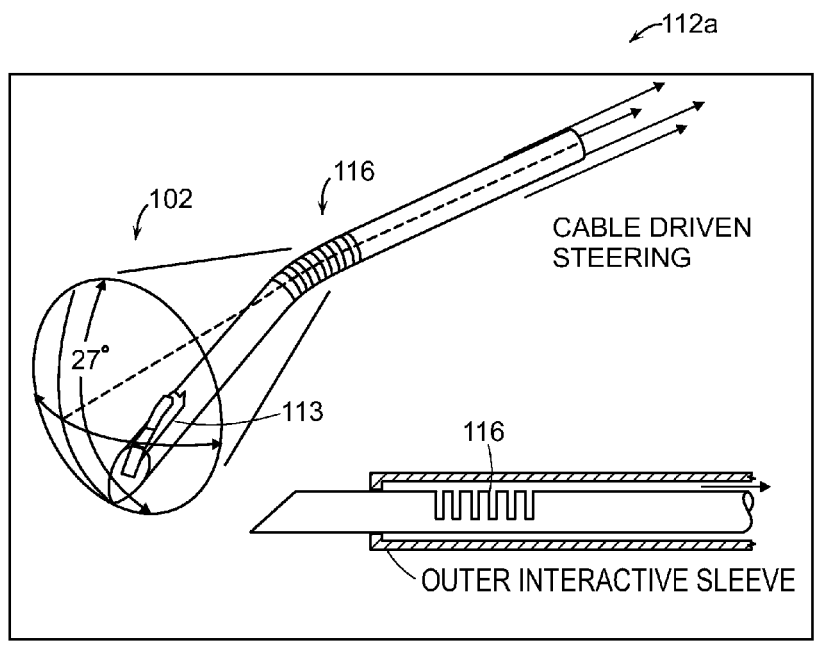
Figure 2C:
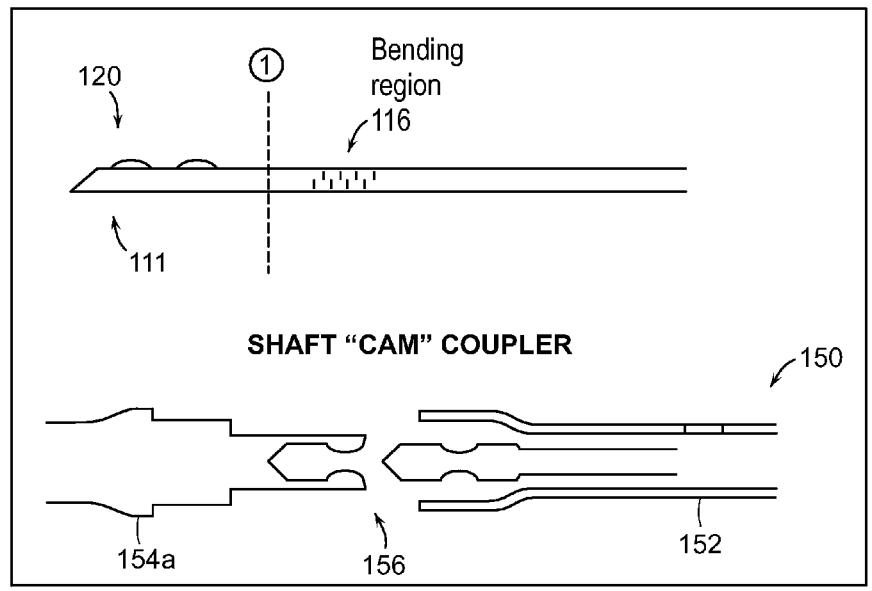
Figure 2D:
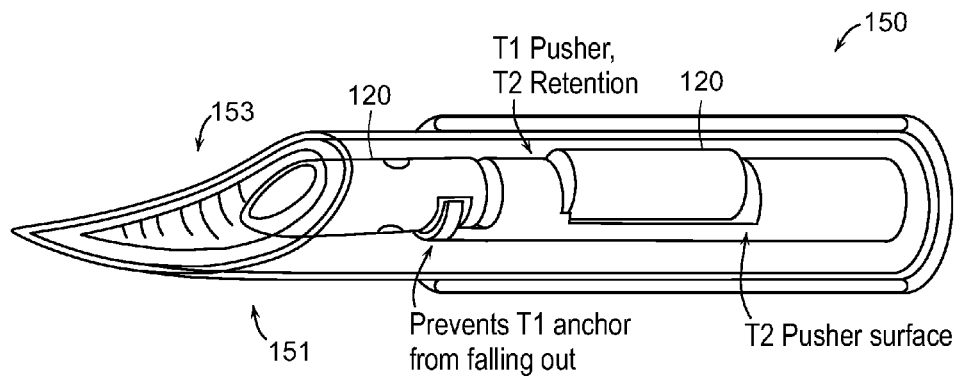

As also illustrated in FIG. 2B, in more particular embodiments the laser cuts are circumferential cuts (i.e., cuts perpendicular to the long axis) that do not extend across the entire cross section of the body member (e.g., partial circumferential cuts). These partial circumferential cuts are such as to allow the body member to bend in either direction with respect to the long axis while maintaining the axial strength of the body member so that the needle portion can be inserted into and through the meniscus allowing deployment of the anchor(s)/implant(s) at the targeted site(s).

Such a first body member also can include a straight region 111 downstream of the flexible portion 116, so that the region of the second body member 150 holding the anchor(s)/implant(s) 120 is disposed in the first body member straight region. Such a straight region also can be arranged so as to include a slotted aperture 113 in which a portion of the anchor(s)/implant(s) may extend outwardly.

The distal end 151 of the second body member 150 also can be configured so as to present a particularly shaped surface or end surface 153 to facilitate insertion of the distal end of the second body member into and through the meniscus. In yet further aspects/embodiments, the second body member can be manipulated so as to extend beyond the distal end of the first body member so as to facilitate insertion of the deployment device distal end into the body and/or knee joint.

A deployment shaft 142 or rod can be disposed within the first body member and coupled to the second body member 150 and the handle assembly 104. The deployment shaft is coupled to the second body member so that the second body member distal end can be inserted into and through the meniscus so as to locate the anchor/implant on the backside of the meniscus and to withdraw the second body member distal end from the meniscus so that another anchor/implant can be deployed. If all anchor/implants are deployed, then the deployment shaft can draw the second body member back within the first body member and so the deployment device can be withdrawn from the knee joint/body.

The handle assembly also can include another mechanism 140 that allows the surgeon to perform the above described actions for the second body member distal end. For example, the deployment shaft 142 can be operably coupled to the another mechanism 140 which can be manipulated so as to move the deployment shaft or rod in the desired direction.

It should be recognized that the foregoing describes one mechanism or structure for allowing the first body member and thus the second body member to be curved or bent in situ during the process of insertion. The foregoing is not limiting as there are other embodiments contemplated for use in the invention and related methods some of which are described hereinafter.

In further embodiments, such a deployment device 100 is configurable so as to also provide a mechanism that can rotate the second body member 150, whereby the needle portion 154 or the portion extending into the meniscus can be rotated so that the distal end 153 (e.g., sharp distal end) thereof entering into the meniscus is oriented to minimize damage to tissue and/or to facilitate insertion of the distal end into and through the meniscus. As also indicated above, such a rotating mechanism is operably coupled to the second body member so that the second body member can be rotated about its long axis. Such a rotating mechanism can be embodied in the handle assembly 104. Such a rotating mechanism also allows the surgeon to selectively rotate the second body member distal end so that the particularly arranged end surface thereof is arranged or orientated in a manner that is appropriate for insertion of the distal end into the meniscus or other tissue of the body.

In particular embodiments, the rotating mechanism includes a knob 130 that is rotatably mounted on the handle assembly 104 and coupled to second body member. In this way, the surgeon can rotate the second body member and thereby the second body member distal end by rotating the knob 130.

In yet further embodiments (see FIG. 2B), the deployment device 100 can further include a cannula that extends outwardly from the handle assembly 104 and about the first body member 110.

In more particular aspects/embodiments, the first member 110 further includes one or more of the following: a proximal and distal end; a flexible portion 116 that is configured to allow the first member to have the one or more geometries more specifically, a flexible portion that is configured to allow the first member to be curved, bent or moved in a first direction (e.g., first arcuate direction) or in a second direction opposite to the first direction.

In more particular aspects/embodiments, the second member further includes one or more of the following: a proximal and distal end; a distal end that is configured for insertion into tissue (e.g., meniscus) of the patient's body; a distal end portion that is configured so that one or more anchor(s)/implant(s) is/are removable received thereon.

In more particular aspects/embodiments, the second member 150 is coupled to the first member and both members are configured such that movement (e.g., curving, bending or other movement) of the first member flexible portion 116 with respect to the longitudinal axis is imparted to the second member 150 thereby causing the second member to move in the direction of the first member; and such coupling of the first and second members is such that the extent of movement in the given direction of the second member is related to the extent of movement of the first member with respect to the longitudinal axis.

In more particular aspects/embodiments the mechanism that is operably coupled or connected to the first member, is such as to allow the first member to have the straight geometry, the curved or bent geometry in a first direction and the curved or bent geometry in a second direction, the second direction being different from or opposite to the first direction. More specifically, such a mechanism is configured so as to allow the surgeon to selectively control the geometry of the first member as well as the extent of the curving or bending in either the first and second directions. In this way, the mechanism allows the surgeon to establish the geometry of the first member and thus the second member as the two members are being inserted in the patient's body and the knee joint.

The mechanism also allows the surgeon to modify the geometry after the first member has been inserted to within the body/knee joint (e.g., a position within the body/knee joint) so that the respective first member and second member distal ends can be thereafter navigated so as to be located proximal the tissue/meniscus at the targeted are. It should be recognized that the deployment device is configurable so that the geometry can be altered a plurality of times after insertion into the knee joint. In more specific aspects/embodiments, the mechanism is a mechanism configurable for curving or bending the first member flexible portion.

Figure 3A:
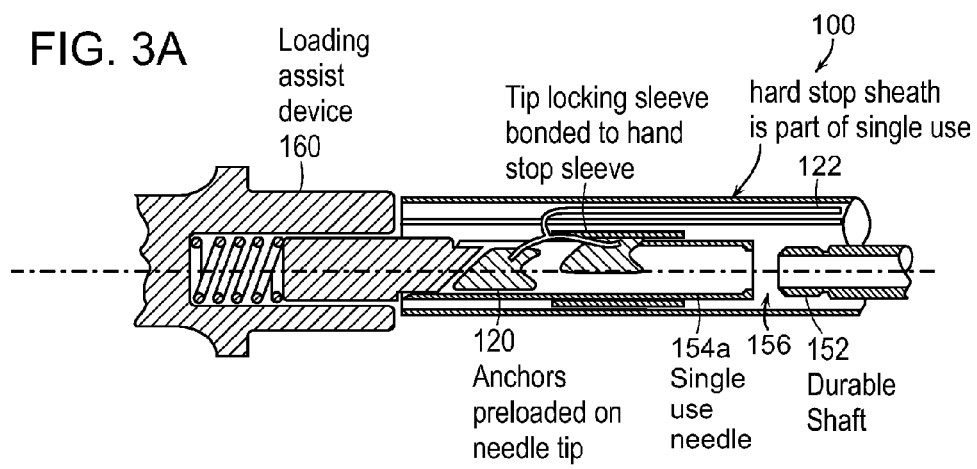
FIG. 3A is a cross-sectional view illustrative of the distal end of a deployment device when coupled to a re-load device.

As indicated herein, in yet further embodiments, the deployment device is configurable so as to make the needle portion 154 of the deployment device replaceable so as to allow the deployment device to be reloaded with new anchors/implants 120 thereby making other portions of the deployment device reusable during a given procedure. Reference shall be made to FIG. 3A which shows a cross-sectional view illustrative of the distal end of a deployment device when coupled to a re-load device 160 and FIG. 3B which shows an illustrative view illustrating the process of re-loading a deployment device with a new needle portion having anchors/implants for deployment, in the following discussion.

Such a deployment device 100 can further include a disposable needle tip 154a or cartridge that carries the anchor(s)/implant(s) for deployment and a body member 152 (e.g., shaft) to which the disposable needle tip is removably secured. In further embodiments, the respective mating ends of the needle tip portion 154a and the body member 152 also are configurable so that they can be removable mated to each other such as for example by a shaft cam coupling 156. In this way, a portion of the deployment device including the handle assembly 104 can be re-used during a procedure for a given patient. The disposable needle tip portion 154a can be used to in effect re-load the deployment device so that it can deploy additional anchor/implants.

The anchors/implants are typically provided with sutures 122 for securing the anchors/implants and the tissue. Once the procedure is completed the deployment device and any used disposable needle tips can be disposed of in accordance with accepted practices. In this way, costs can be minimized as a portion of the deployment can be re-used during the procedure.

Figure 3B:
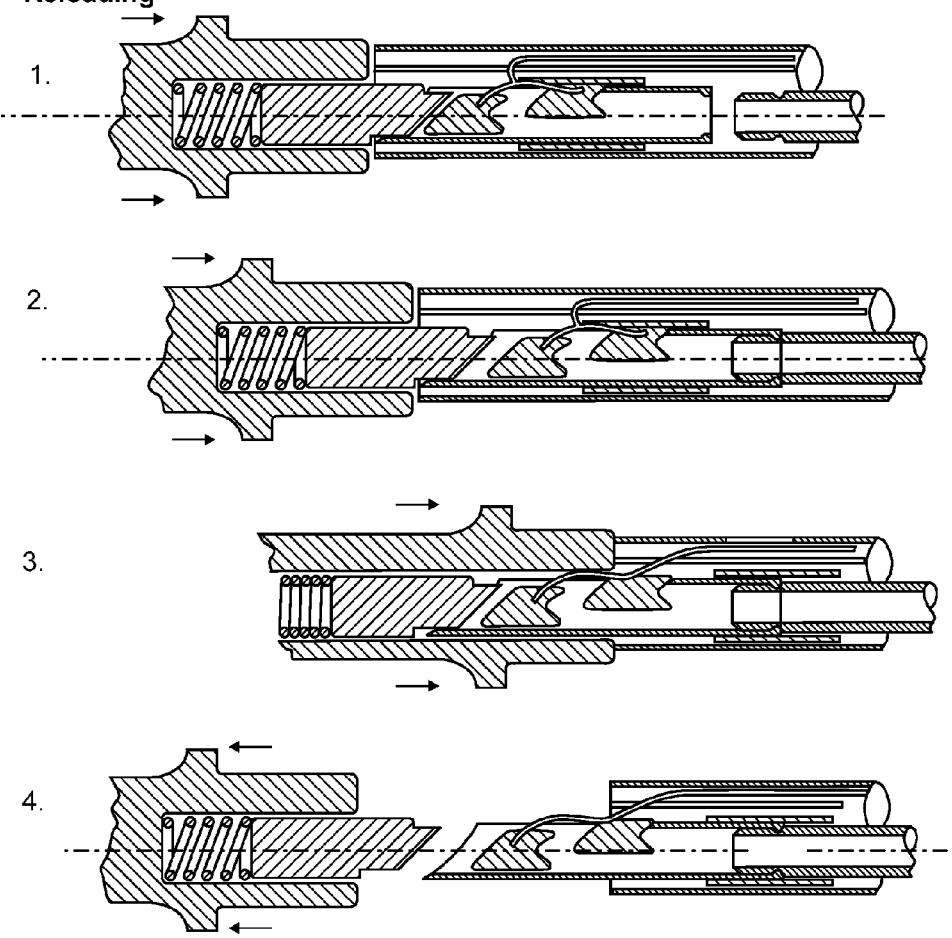
FIG. 3B is an illustrative view illustrating the process of re-loading a deployment device with a new needle portion having anchors/implants for deployment.
Figure 4A:
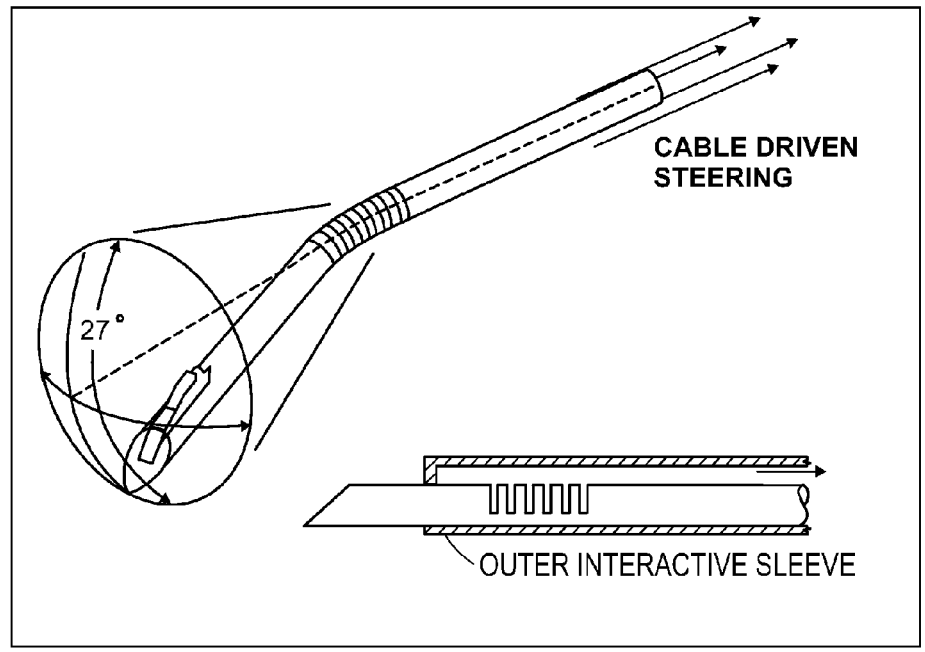
Figure 4B:
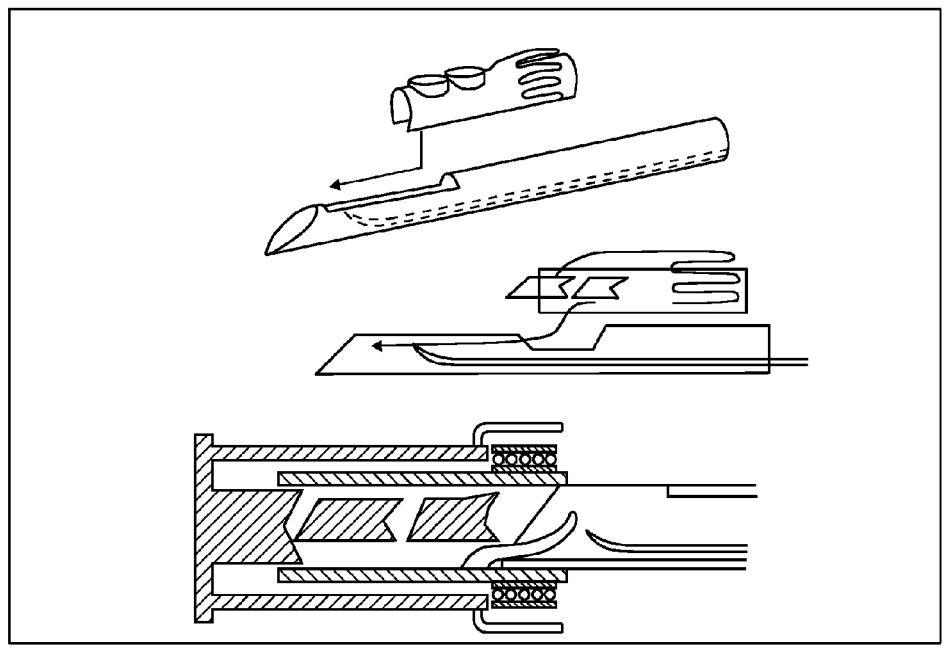
Figure 4D:
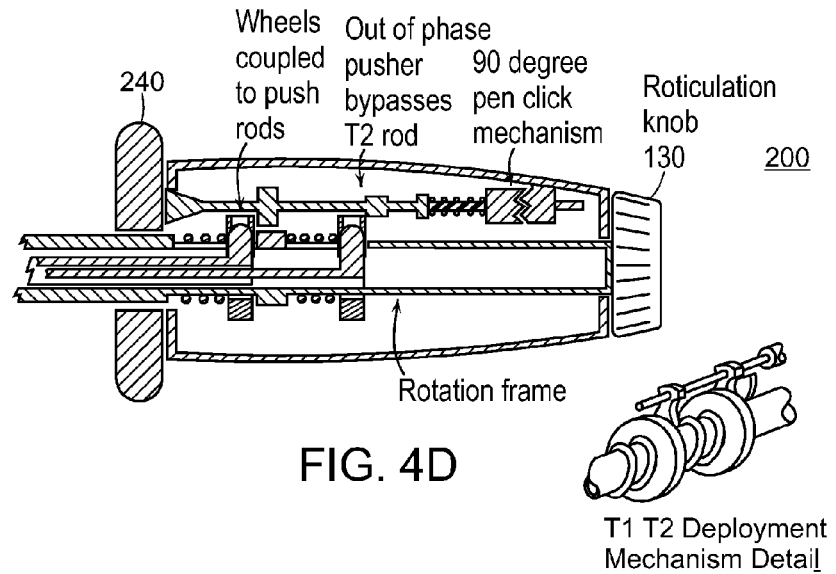
Figure 4E:
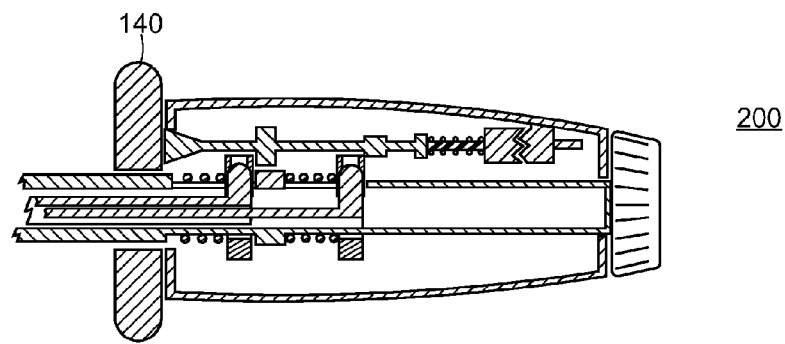
Figure 4F:
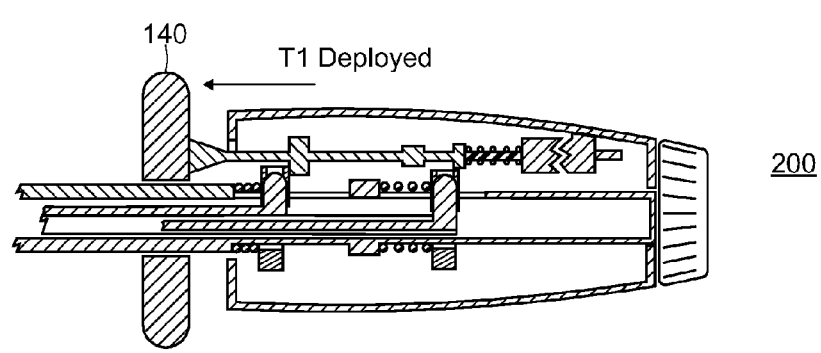
Figure 6E:
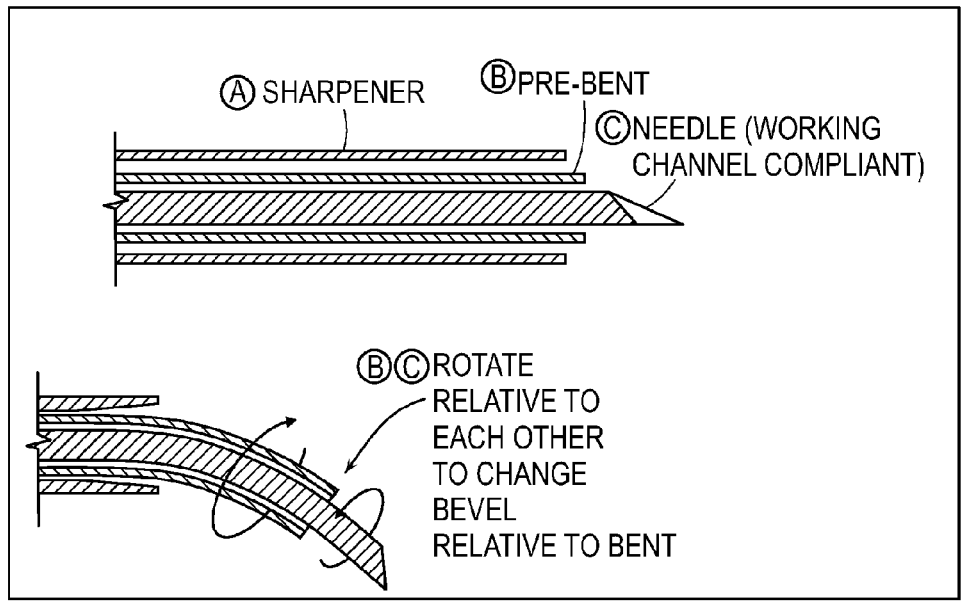
Figure 6F:
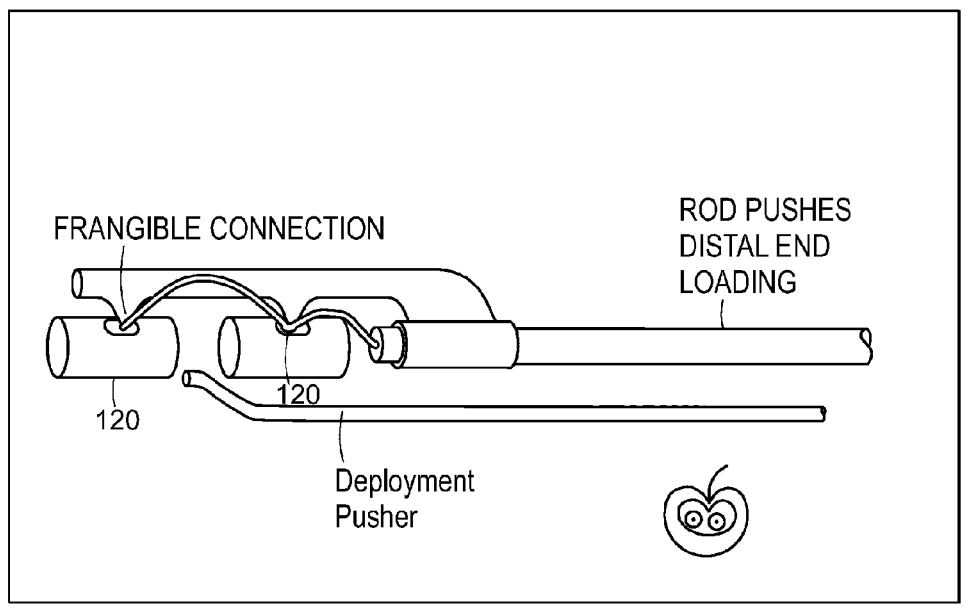

In use, a loading assist device 160 including for example a pushing member and a spring is positioned at the distal end of the disposable needle tip portion 154a so that the pushing member is in contact with the distal end. As illustrated in FIG. 3B, the loading assist device is pushed in a direction so as to cause the needle tip portion 154a and the body member 152 to couple with each other. Thereafter, the loading assist device 160 is removed so that the thus re-loaded deployment device can be continued to be used in the surgical procedure.

In yet further embodiments, the deployment device can further include a cannula that extends outwardly from the handle device and about the first body member.

Referring now to FIGS. 4A-F there are shown various views of an anchor/implant deployment device 200 according to a second aspect of the present invention. This deployment device 200 utilizes a cable pull mechanism to cause the first body member to flex and be adjustable during a surgical procedure as well as using the rotating mechanism to separately deploy each of the anchors/implants (see FIGS. 4D-F). The cable pull mechanism also is such as to control the amount of bending or curving.

Referring now to FIG. 5, there is shown a cross-sectional view illustrative of the distal end of the deployment device 200 of FIGS. 4A-F when coupled to a re-load device. As shown, the deployment device 200 according to this aspect of the invention also is configured and arranged to that the disposable needle tip portion 154a can be removed and replaced with a new needle tip containing anchors/implants. In other words, the deployment device according to this aspect of the present invention can be re-loaded with a new set of implants after the first repair is completed.

Referring now to FIGS. 6A-F there is shown various views of an anchor/implant deployment device 300 according to a third aspect of the present invention. According to this aspect a pre-bent cannula 380 is disposed about the first body member outer surface 310 and extends along the length of the first body member. In particular embodiments, the pre-bent cannula 380 is maintained in a straight condition before it is deployed and also is made of a material which returns to the bent condition as it deploys from the handle assembly. This bending of the cannula is imparted to the first body member 310 and thus the second body member 320 thereby causing the two body members to bend in the direction and to the extent dictated by the pre-bent cannula.

In further embodiments, the deployment device 300 is arranged with two pusher members 390a, b that are nested. In use the first pusher 390a is arranged so that it causes one of the anchor/implants 120 to be deployed and the second pusher 390b causes the other of the anchor/implant 120 to be deployed.

In yet further embodiments, the handle assembly 704 is configured so as to include a plurality of such pre-bent cannulas and a mechanism for allowing the surgeon to select one of the plurality of pre-bent cannulas for deployment. In this way, the surgeon can selectively control the in situ bending of the body member by selecting the cannula.

Figure 7A:
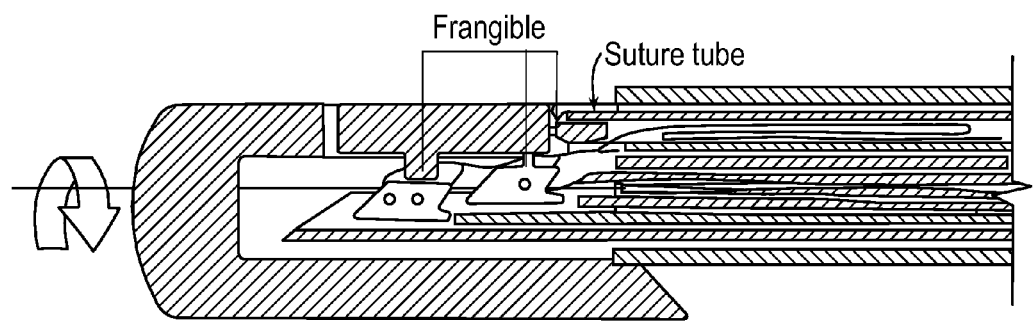
FIGS. 7A, B are various views illustrating reloading of the deployment device of FIGS. 6A-F, where
Figure 7B:
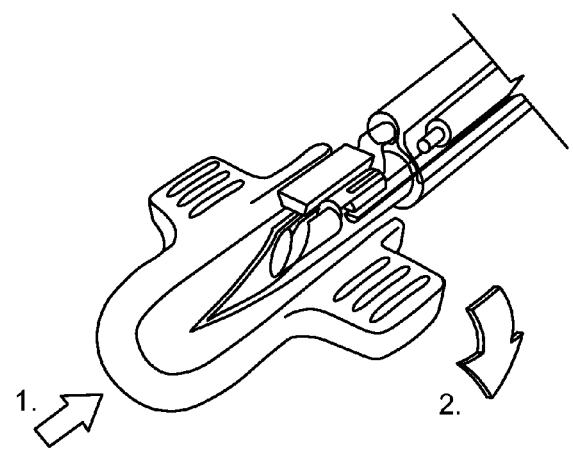
FIG. 7B is a further illustration of the re-load device.
Figure 8D:
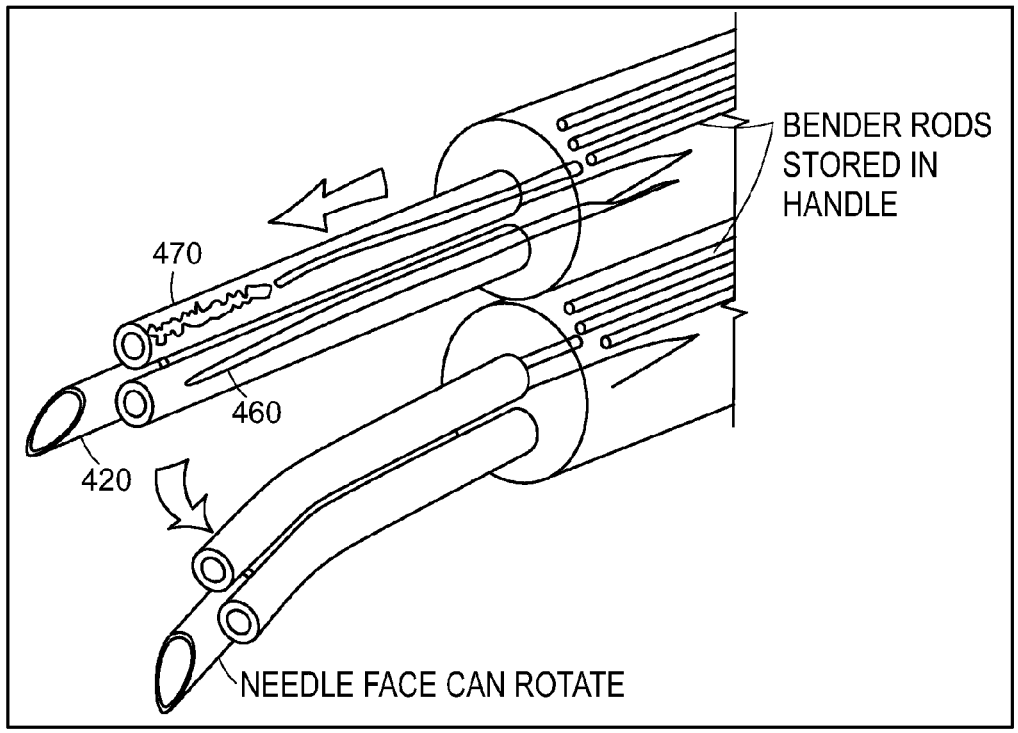
Figure 8E:
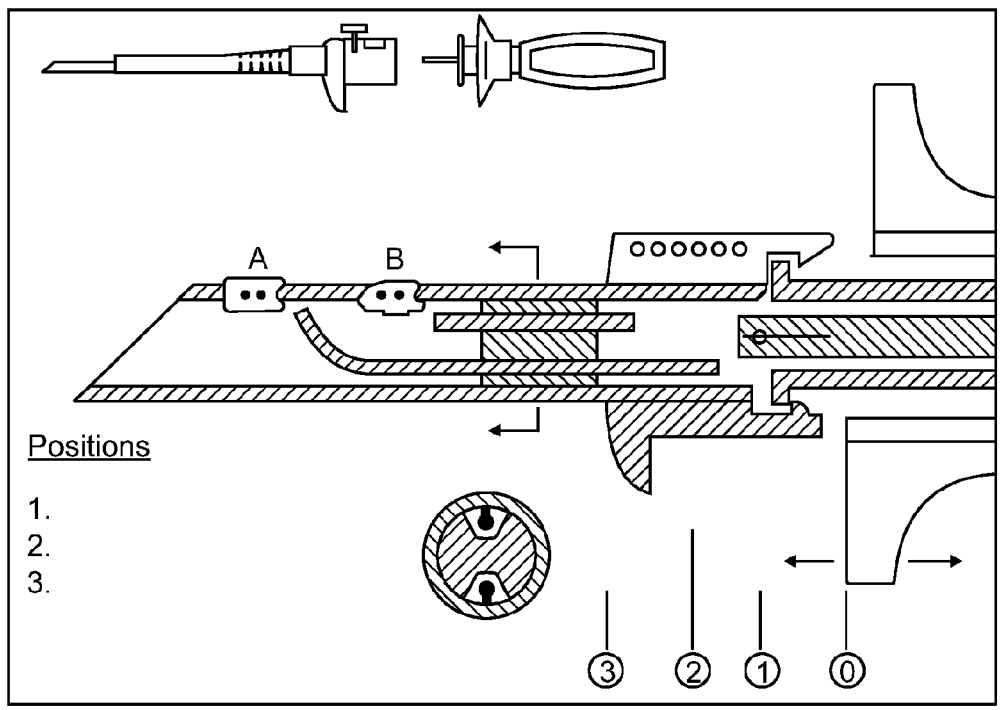

Referring now to FIG. 7A there is shown a cross-sectional view illustrative of the distal end of the deployment device 300 of FIGS. 4A-F when coupled to a re-load device as further shown in FIG. 7B. As shown, the deployment device 300 according to this aspect of the invention also is configured and arranged to that the particular needle tip portion of the deployment device 300 can be removed and replaced with a new needle tip portion containing anchors/implants. In other words, the deployment device 300 according to this aspect of the present invention can be re-loaded with a new set of implants after the first repair is completed.

Referring now to FIGS. 8A-E there is shown various views of an anchor/implant deployment device 400 according to a fourth aspect of the present invention. According to this aspect, a tubular member 470 is connected or coupled to the outer surface of the first body member 410 that extends along the length of the first body member. In use, a pre-bent rod 472 is inserted (pre-use) into the tubular member 410 from its stored straight condition and which rod bends as it deploys into the tubular member. This bending movement of the rod is thereby also imparted to the first and second body members 410, 420 thereby causing the second body member to bend in the direction and extent dictated by the pre-bent rod. In yet further embodiments (see FIGS. 8B-C), the handle assembly 404 is configured so as to include a plurality of such pre-bent rods and a mechanism for allowing the surgeon to select one of the plurality of rods for deployment. For example, the plurality of rods can be assembled radially about the long axis (see FIG. 8C) so that the surgeon can select one of the rods by rotating the assembly of rods. In this way, the surgeon can selectively control the in situ bending of the body member. The handle assembly also can include a mechanism that can maintain the "pre-bent rods" in a straight condition until deployed.

Figure 9:
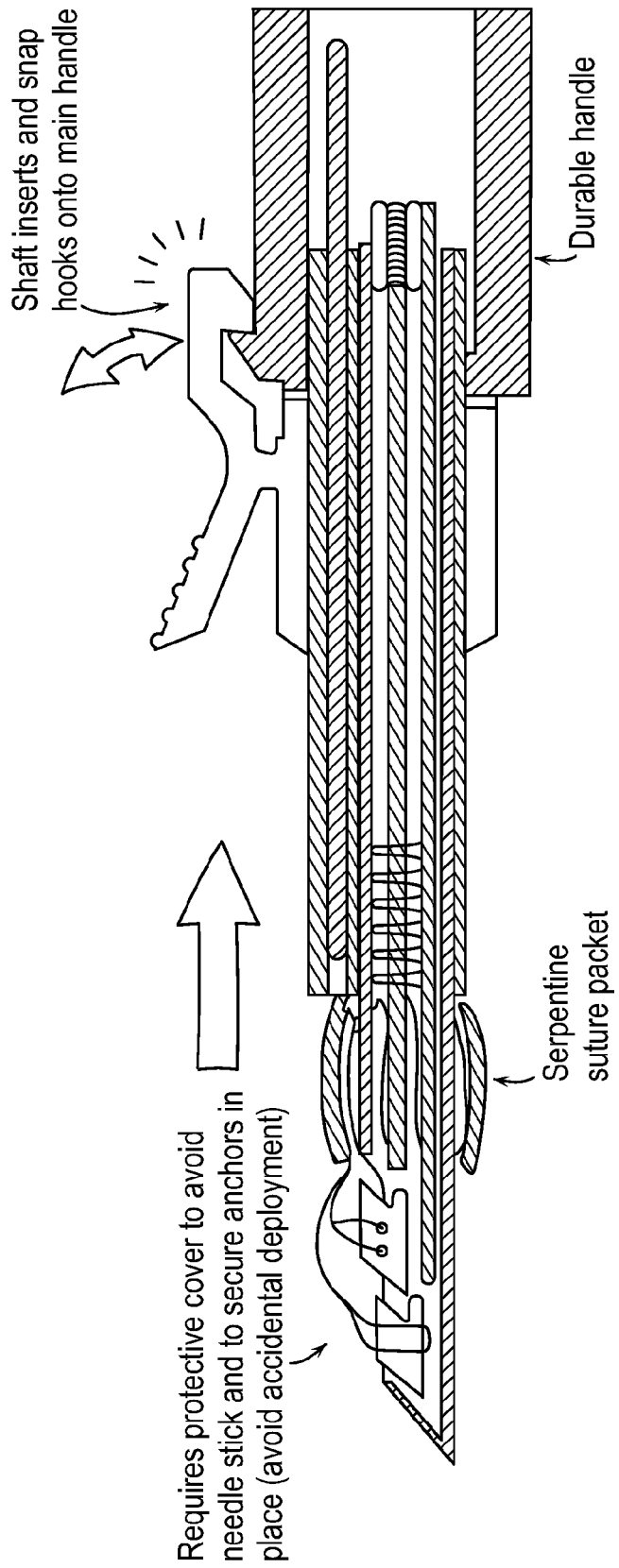
FIG. 9 is an illustrative cross sectional view of the distal end of the deployment device of FIGS. 8A-E when re-loaded with a new needle shaft.

Referring now to FIG. 9 there is shown a cross-sectional view illustrative of the distal end of the deployment device 400 of FIGS. 8A-F. As shown, the deployment device 400 would have a replaceable shaft with implants. In use, the used shaft is removed and discarded after the initial repair is completed. Thereafter, another shaft with implants would be loaded onto the deployment device 400 as illustrated in FIG. 9. In other words, the deployment device 400 according to this aspect of the present invention can be re-loaded with a new set of implants after the first repair is completed.

As indicated herein the present invention also features methods for repairing tissue such as the meniscus using such a deployment device and manipulating such a device so that each anchor/implant can be navigated to a targeted location(s) and deployed from the deployment device so that it appropriately resides in or proximal the tissue (e.g., resides along the backside of the meniscus at the targeted location). More specifically, such inventive methods include repairing the meniscus using the above described deployment device(s).

In illustrative embodiments, such a methodology includes preparing the deployment device for use in accordance with the desired surgical procedure. More particularly, one would make sure that the deployment device was loaded with anchors/implants (e.g., suture anchors) so that they could be deployed during the surgical procedure.

Also, the surgeon would determine the desired end geometry for the distal end of the deployment device for at least insertion into the body such as the knee joint. If the desired end geometry is different from the geometry being initially presented, the surgeon would take the appropriate actions to adjust the end geometry to correspond to the desired end geometry. In yet further embodiments, the end geometry would be controlled so that it does not vary substantially as the distal end of the deployment device is being inserted into the body/knee joint.

After inserting the deployment device into the body, the surgeon manipulates the deployment device, more particularly the hand assembly thereof, to navigate the deployment device. Such navigating is undertaken so that the distal end will arrive at a targeted location or area while at the same time minimizing the potential for damage to surrounding tissue or body parts.

During such insertion and manipulation, the surgeon continues to assess the need for further adjusting the end geometry so that the distal end will arrive at the targeted location or area. In other words, the surgeon assesses the need for adjusting the end geometry again so that the distal end will arrive at the targeted location or area. It should be recognized that the surgeon can make such an assessment, for example, after inserting the deployment device a predetermined distance into the body, after insertion to a predetermined location within the body, or continuously. Also, it is contemplated that the surgeon can make one or more such further adjustments during such insertion and manipulation of the deployment device.

This insertion, manipulation and adjustment process is continued until the distal end is navigated to the targeted area or location. In the case of a meniscus for example, navigation to the location of a tear in the meniscus. Following such locating of the distal end, the surgeon then takes the appropriate actions for deploying an anchor/implant at or proximal that location. For example, in the case of a meniscus repair, the surgeon would pass the needle portion through the meniscal tissue to the backside of the meniscus. Thereafter, the surgeon would deploy the anchor/implant either passively or actively so that the anchor is disposed along the back side of the meniscus.

After so deploying an anchor/implant, the surgeon would then determine if another anchor/implant is to be deployed according to the procedure. If yes, then the surgeon would take the appropriate actions to deploy the next anchor/implant. For example, in the case of meniscus repair, the surgeon would remove the inserted needle portion from the meniscus, navigate to another targeted location repeat the deployment process. If the deployment process is completed, then the surgeon would remove the deployment device and continue on with the repair procedure.

In further embodiments, if the deployment process is not completed and the deployment device does not have any more anchors/implants for deployment, then the surgeon would remove the used deployment device from the body. In some cases, the complete repair process involves performing one or more individual tissue repairs which can involve implanting a plurality or a multiplicity of anchor/implant pairs. The surgeon could then either obtain a new loaded deployment device or as provided by the present invention, the surgeon could remove the spent needle portion from the deployment device and replace it with a new loaded needle portion. Thereafter the surgeon could repeat the above-described process. In such cases, the surgeon may perform certain parts of the surgical procedure such as to secure the deployed anchors/implants in place before proceeding with the deployment of any additional anchors/implants.

The foregoing is illustrative and shall not be considered as being exhaustive or inclusive of all surgical procedures that involve the use of deploying anchors/implants to treat damaged tissue.

Although preferred embodiments of the invention have been described using specific terms, such description is for illustrative purposes only, and it is to be understood that changes and variations may be made without departing from the spirit or scope of the following claims.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A deployment device for deploying an anchor/implant for treating damaged tissue, said deployment device comprising:
    a first member comprising:
        a proximal end, a distal end, and a longitudinal axis extending therebetween;
        a flexible portion extending along the longitudinal axis between the proximal end and the distal end; and
        a lumen extending along the longitudinal axis;
    a second member moveably disposed within the lumen; and a moving mechanism operably coupled to the first member, said moving mechanism configured to move the flexible portion to have one of a plurality of geometries and to control an extent or amount of movement of the flexible portion;
    wherein the second member includes a distal end portion removeably secured to a shaft member portion, the distal end portion configured to carry one or more anchors/implants for deployment;
    wherein the distal end portion is removeably secured to the shaft member portion such that a used end portion where the anchors/implants have been deployed can be removed and replaced by a new end portion which has new anchors/implants to be deployed.

2. The deployment device of claim 1, wherein the moving mechanism is arranged so that such moving of the flexible portion occurs one of external to a body or in-situ within the body.

3. The deployment device of claim 1, wherein the plurality of geometries include a straight geometry, a first bending geometry that bends in a first direction, a second bending geometry that bends in a second direction different from the first direction, a first curved geometry that curves in a first direction, and a second curved geometry that curves in a second direction different from the first direction.

4. The deployment device of claim 3, wherein the moving mechanism is further configured to control an extent or amount of bending or curving of the flexible portion and to maintain the straight geometry of the flexible portion.

5. The deployment device of claim 1, wherein:
    the second member is coupled to the first member; and
    the first and second members are configured and arranged such that movement of the flexible portion with respect to the longitudinal axis is imparted to the second member, thereby causing the second member to move in a direction of the first member.

6. The deployment device of claim 5, wherein an extent of the movement of the second member is related to an extent of the movement of the flexible portion with respect to the longitudinal axis.

7. The deployment device of claim 1, wherein the moving mechanism includes a rod that is secured to the first member and which rod is arranged so that it extends along a length of the first member and so as to be disposed off-axis from the longitudinal axis of the first member.

8. The deployment device of claim 7, wherein the moving mechanism further includes a manipulation device that is operably coupled to the rod and arranged so that movement of the manipulation device in a given direction causes the rod to move axially and thus move the first member.

9. The deployment device of claim 8, wherein the movement of the rod in one direction causes the flexible portion to present one geometry of the plurality of geometries and the movement of the rod in a second direction causes the flexible portion to present a second geometry of the plurality of geometries.

10. The deployment device of claim 1, further comprising a rotation device being operably coupled to the second member such that operation of the rotation device causes a distal end of the second member to be rotated about a long axis such that the distal end is orientated in a desired angular orientation.

* * * * *